United States Patent

Berg et al.

[11] Patent Number: 6,106,454
[45] Date of Patent: Aug. 22, 2000

[54] MEDICAL DEVICE FOR DELIVERING LOCALIZED RADIATION

[75] Inventors: Eric P. Berg, Plymouth; Thomas Q. Dinh, Minnetonka, both of Minn.

[73] Assignee: Medtronic, Inc., Minneapolis, Minn.

[21] Appl. No.: 08/877,426

[22] Filed: Jun. 17, 1997

[51] Int. Cl.$^7$ .............................. A61B 17/00; A61B 5/00
[52] U.S. Cl. .................................................................. 600/3
[58] Field of Search .............................. 600/1–8; 376/156

[56] References Cited

U.S. PATENT DOCUMENTS

| | | |
|---|---|---|
| 3,105,492 | 10/1963 | Jeckel . |
| 3,425,418 | 2/1969 | Chvapil et al. . |
| 3,451,996 | 6/1969 | Sumyk et al. . |
| 3,523,807 | 8/1970 | Gerendas . |
| 3,549,409 | 12/1970 | Dyck . |
| 3,688,317 | 9/1972 | Kurtz . |
| 4,188,188 | 2/1980 | Willner et al. . |
| 4,229,540 | 10/1980 | Coan . |
| 4,229,838 | 10/1980 | Mano . |
| 4,321,711 | 3/1982 | Mano . |
| 4,540,573 | 9/1985 | Neurath et al. . |
| 4,548,736 | 10/1985 | Müller et al. . |
| 4,613,665 | 9/1986 | Larm . |

(List continued on next page.)

FOREIGN PATENT DOCUMENTS

| | | |
|---|---|---|
| 0 366 564 A2 | 10/1989 | European Pat. Off. . |
| WO 86/06729 | 11/1986 | WIPO . |
| WO 89/07932 | 8/1989 | WIPO . |
| 9112779 | 9/1991 | WIPO . |
| WO 94/17108 | 8/1994 | WIPO . |

OTHER PUBLICATIONS van Beusekom et al Circulation86(supp.l):1–731, 1992.

Lincoff et al. *J.Am. Coll Cardiol* 21(sup.1):335A, Dec. 1994.

Fischell et al., "Low–Dose β–Particle Emission From 'Stent' Wire Results in Complete, Localized Inhibiton of Smooth Muscle Cell Proliferation", *Circulation* 90:2956–2963 (1994).

Waksman et al., "Endovascular Low–Dose Irradiation Inhibits Neointima Formation After Coronary Artery Balloon Injury in Swine. A Possible Role for Radiation Therapy in Restenosis Prevention", *Circulation, 91*:1533–1539 (1995).

Dyck, "Inorganic Heparin Complexes for the Preparation of Nonthrombogenic Surfaces", *J. Biomed. Mater. Res.*, 6, pp. 115–141 (1972).

Liu et al., "Porous polyurethane vascular prostheses with variable compliances", *J. Biomed. Mater. Res.*, 26, pp. 1489–1502 (1992).

McNair, "Using Hydrogel Polymers for Drug Delivery", *Medical Device Technology*, pp. 16–22, (1996).

"Photolink Surface Modifications Technical Bulletin: Heparin Coatings For Medical Devices", *Brochure from BSI Surface Modification Sciences*, (1994).

William D. Spotnitz et al., "Fibrin Glue from Stored Human Plasma. An Inexpensive and Efficient Method for Local Blood Bank Preparation", *The American Surgeon*, 53, 46–462 (1987).

K. Whang et al., "A novel method to fabricate bioabsorable scaffolds", *Polymer*, 36:4, 837–842 (1995).

*Primary Examiner*—Samuel G. Gilbert

[57] ABSTRACT

A medical device useful for localized delivery of radiation in vivo is provided. The medical device includes a structure including a porous material; and a plurality of discrete particles including a water-insoluble radioactive salt dispersed throughout a substantial portion of the porous material. The water-insoluble radioactive salt is formed by contacting an aqueous radioactive salt solution with a heavy metal water-soluble salt dispersed throughout a substantial portion of the porous material. The heavy metal water-soluble salt can be dispersed in the porous material so that the device can be sterilized and the radioactive material can be loaded in the device in situ, for example, just prior to implantation.

8 Claims, 2 Drawing Sheets

U.S. PATENT DOCUMENTS

| | | |
|---|---|---|
| 4,623,539 | 11/1986 | Tunc . |
| 4,680,177 | 7/1987 | Gray et al. . |
| 4,733,665 | 3/1988 | Palmaz . |
| 4,768,507 | 9/1988 | Fischell et al. . |
| 4,800,882 | 1/1989 | Gianturco . |
| 4,873,308 | 10/1989 | Coury et al. . |
| 4,886,062 | 12/1989 | Wiktor . |
| 5,010,063 | 4/1991 | Piani et al. . |
| 5,039,529 | 8/1991 | Bergendal et al. . |
| 5,059,166 | 10/1991 | Fischell et al. . |
| 5,061,276 | 10/1991 | Tu et al. . |
| 5,104,860 | 4/1992 | Piani et al. . |
| 5,342,605 | 8/1994 | Illig . |
| 5,352,434 | 10/1994 | Illig et al. . |
| 5,399,318 | 3/1995 | Mancilla et al. . |
| 5,464,650 | 11/1995 | Berg et al. . |
| 5,510,077 | 4/1996 | Dinh et al. . |
| 5,531,735 | 7/1996 | Thompson . |
| 5,541,305 | 7/1996 | Yokota et al. . |
| 5,541,424 | 7/1996 | Solomon et al. . |
| 5,554,182 | 9/1996 | Dinh et al. . |
| 5,571,166 | 11/1996 | Dinh et al. . |
| 5,591,227 | 1/1997 | Dinh et al. . |
| 5,599,352 | 2/1997 | Dinh et al. . |
| 5,609,629 | 3/1997 | Fearnot et al. . |
| 5,624,411 | 4/1997 | Tuch . |
| 5,679,400 | 10/1997 | Tuch . |
| 5,697,967 | 12/1997 | Dinh et al. . |
| 5,716,981 | 2/1998 | Hunter et al. . |
| 5,722,984 | 3/1998 | Fischell et al. ............................ 600/3 |
| 5,776,184 | 7/1998 | Tuch . |
| 5,848,995 | 12/1998 | Walder . |
| 5,873,811 | 2/1999 | Wang et al. ............................... 600/5 |
| 5,919,126 | 7/1999 | Armini ....................................... 600/3 |
| 5,942,209 | 8/1999 | Leavitt et al. ......................... 424/1.25 |

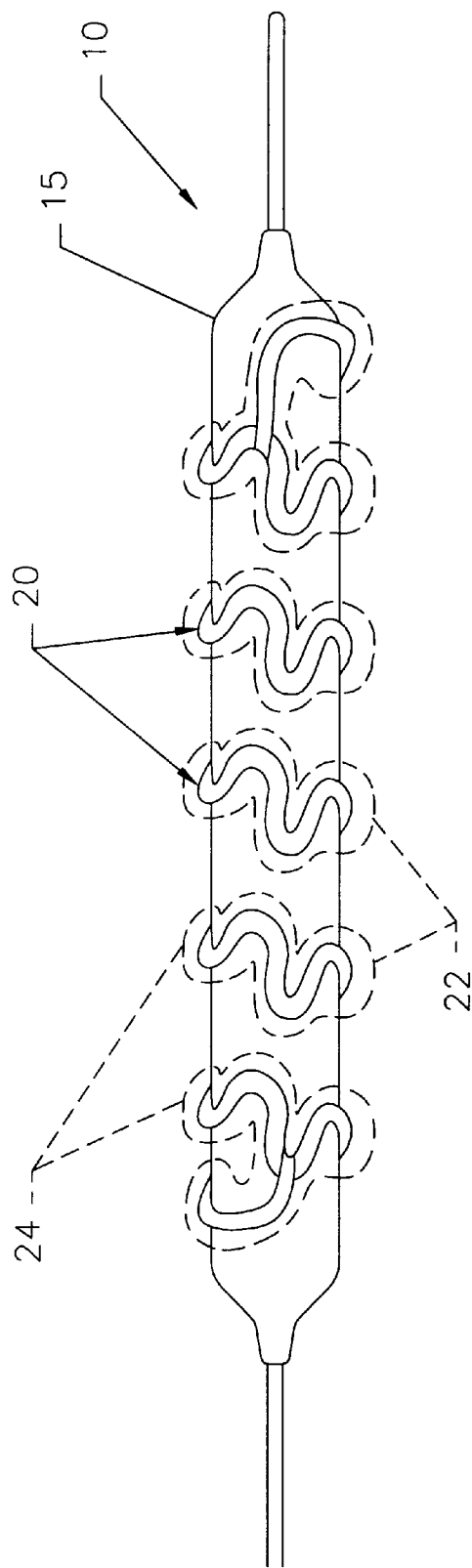
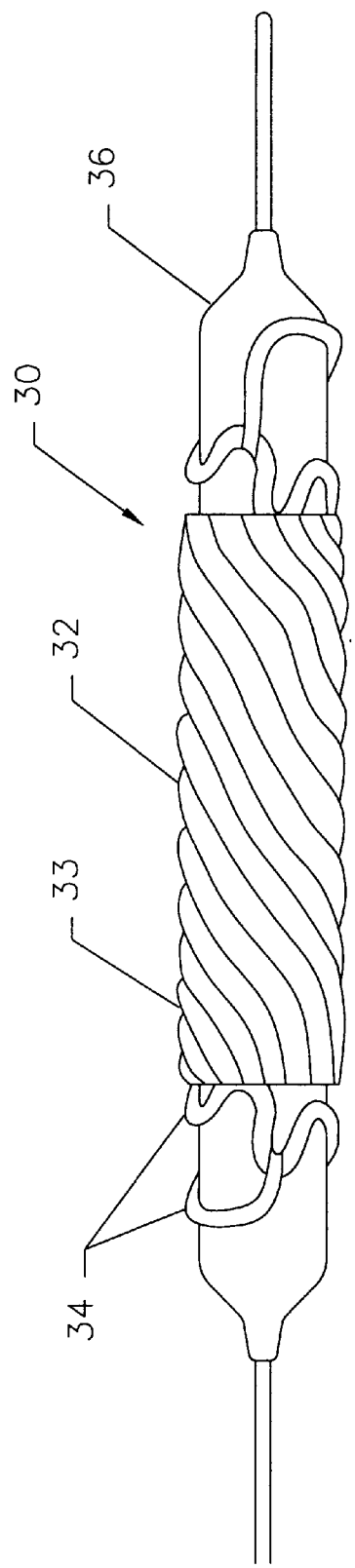
FIG.1
FIG.2

MEDICAL DEVICE FOR DELIVERING LOCALIZED RADIATION

FIELD OF THE INVENTION

This invention relates to a medical device for delivering localized radiation in vivo, for example in an arterial site treated with percutaneous transluminal coronary angioplasty therapy for obstructive coronary artery disease or in a site after atherectomy. Also provided is a method for making a medical device capable of delivering localized radiation in vivo.

RELATED ART

Stenosis is a narrowing or constriction of a duct or canal. A variety of disease processes, such as atherosclerotic lesions, immunological reactions, congenital abnormalities, and the like, can lead to stenosis of arteries or ducts. In the case of stenosis of a coronary artery, this typically leads to myocardial ischema. Percutaneous transluminal coronary angioplasty (PTCA), the insertion and inflation of a balloon catheter into a stenotic vessel to affect its repair is widely accepted as an option in the treatment of obstructive coronary artery disease. Other vascular invasive therapies include atherectomy (mechanical systems to remove plaque residing inside an artery), laser ablative therapy and the like. However, restenosis at the site of a prior invasive coronary artery disease therapy occurs in a majority of cases. Restenosis, defined angiographically, is the recurrence of a 50% or greater narrowing of a luminal diameter at the site of a prior coronary artery disease therapy, such as a balloon dilatation in the case of PTCA therapy. Restenosis is a major problem which limits the long-term efficacy of invasive coronary disease therapies. In particular, an intra-luminal component of restenosis develops near the end of the healing process initiated by vascular injury, which then contributes to the narrowing of the luminal diameter. This phenomenon is sometimes referred to as "intimal hyperplasia." In some instances, restenosis develops so rapidly that it may be considered a form of accelerated atherosclerosis induced by injury. Additionally, the rapid onset of restenosis is compounded by the lack of predictability to determine which patients, vessels, or lesions will undergo restenosis.

Although the mechanism of restenosis is not fully understood, clinical evidence suggests that restenosis results from a migration and rapid proliferation of a subset of predominately medially derived smooth muscle cells which is apparently induced by the injury caused by the invasive therapy. Such injury, for example, is caused by the angioplasty procedure when the balloon catheter is inflated and exerts pressure against the artery wall, resulting in media tearing. It is known that smooth muscle cells proliferate in response to mechanical stretch and stimulation by a variety of growth factors. It is believed that such proliferation stops one to two months after the initial invasive therapy procedure but that these cells continue to express an extracellular matrix of collagen, elastin and proteoglycans. Additionally, animal studies have shown that after balloon injury, denudation of endothelial cells occurs, followed by platelet adhesion and aggregation, and the release of platelet-derived growth factor (PDGF) as well as other growth factors. As mentioned above, this mass of tissue contributes in the re-narrowing of the vascular lumen in patients who have restenosis. It is believed that a variety of biologic factors are involved in restenosis, such as the extent of the injury, platelets, inflammatory cells, growth factors, cytokines, endothelial cells, smooth muscle cells, and extracellular matrix production, to name a few.

Attempts to inhibit or diminish restenosis include administration of pharmacological agents, such as aspirin, anti-platelet drugs, anticoagulants, corticosteroids, calcium-channel blocker, fish oils, and the like. Success of these agents has been limited. For example, U.S. Pat. No. 4,768,507 (Fischell et al.) describes a stent coated with an anti-thrombogenic agent which may reduce platelet and fibrin deposition. However, this type of therapy does not address the migration and proliferation of smooth muscle cells in response to a vascular injury, as mentioned above. Other methods to diminish restenosis include the delivery of modified viruses, especially adenoviruses, that carry gene sequences capable of ameliorating or preventing the symptoms of cardiovascular disease, such as that described in International Publication No. WO 94/27612 (French et al.).

In searching for alternative therapies which may decrease the likelihood of restenosis, gamma radiation has been shown to limit cell proliferation by arresting cell division thereby reducing the number of clonal progenitors. However, re-injury or other stimuli can induce a response by smooth muscle cells by migration, proliferation and matrix synthesis, as mentioned above. Ionizing radiation has been shown to inhibit thymidine uptake and collagen synthesis by cultured fibroblasts. For example, it has been shown that low doses of superficial x-rays after surgery may prevent hypertrophic scarring and keloid formation which typically results from the excessive formation of collagen after surgical injury. Thus, radiation may inhibit cellular hyperplasia by either killing progenitor cells or limiting their replication.

In the case of restenosis, typically the radiation should be delivered intra-luminally so as to be effective in reducing intimal hyperplasia. For example, U.S. Pat. No. 5,059,166 (Fischell et al.) describes an intra-arterial stent that is fabricated from either a pure metal or a metal alloy which has been irradiated so that is has become radioactive. However, as with any isotopes or radioactive material, the useful life, which includes both the shelf-life and the therapeutic life, of the device is limited by the half-life of the isotope utilized. The shelf-life of any device containing a radioactive material necessarily begins upon attachment of the radioisotope to the device because the radioactive material is continuously decaying. If storage and/or shipping are required, the radioactive material continues to decay to the point where any radiation emitted from the device is negligible. Thus, implantation of the device would not be advantageous.

Furthermore, devices formed from spaced apart radioactive metallic wires, such as stents or guide wires, typically do not deliver a uniform dosage to the internal body site. In general, this is because the radiation emitting materials are not uniformly distributed but are necessarily distributed in a pattern defined by the spaced apart wires of the device itself. The radiation is then delivered in vivo in discrete intervals, also as defined by the spaced apart wires of the device.

What is yet needed is a device for delivering localized radiation to a vascular site, preferably in a substantially uniform manner, typically as defined by the configuration or shape of the device. It is further desired that the radiation emitting material is preferably convenient to administer and should not adversely affect the useful life of the device.

SUMMARY OF THE INVENTION

This invention relates to a device to deliver localized radiation in vivo. Preferably, the device according to the invention is capable of delivering localized radiation to a body lumen to treat or prevent injury. The term "injury"

means a trauma, that may be incidental to surgery or other treatment methods including deployment of a stent, or a biologic disease, such as an immune response or cell proliferation caused by the administration of growth factors. In addition, the methods of the invention may be performed in anticipation of "injury" as a prophylactic. A prophylactic treatment is one that is provided in advance of any symptom of injury in order to prevent injury, prevent progression of injury or attenuate any subsequent onset of a symptom of such injury.

In accordance with the invention, a device for delivering localized radiation includes a structure including a porous material and a plurality of discrete particles of water-insoluble radioactive salt dispersed throughout a substantial portion of the porous material. Preferably, the device is capable of being implanted in a body so that the localized radiation can be delivered in vivo, typically at a site of vascular injury or trauma. More preferably, the porous material is biocompatible, sufficiently tear-resistant and non-thrombogenic.

The porous material may be a film on at least a portion of the structure or the porous material may be an integral portion of the structure. Preferably, the porous material is selected from the group of a natural hydrogel, a synthetic hydrogel, teflon, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like.

The radioactive salt preferably comprises a β-emitting isotope. More preferably, the β-emitting isotope has a half-life of about 150 days or less. Most preferably, the radioactive salt is selected from the group of $AgI^{125}$, $BaS^{35}O_4$, and $(Ca)_3(P^{32}O_4)_2$.

The structure of the device preferably includes a shape which is capable of delivering localized radiation in an internal human body site, such as an artery, vein, urethra, other body lumens, cavities, and the like. In one embodiment, the shape is preferably generally cylindrical, and more preferably, the shape is selected from the group of a catheter, a stent, and a guide wire. In another embodiment, the shape is preferably generally sheet-like.

In another embodiment of the invention, an implantable device capable of delivery of localized radiation in vivo includes a structure comprising a porous material; and a plurality of discrete particles comprising a heavy metal water-soluble salt dispersed throughout a substantial portion of the porous material. Preferably, the heavy metal water-soluble salt is selected from the group of $AgNO_3$, $Ba(NO_3)_2$, $BaCl_2$, and $CaCl_2$. The amount of water-soluble salt dispersed throughout a portion of the porous material determines the total amount of radiation capable of being emitted once the device is implanted.

The invention also provides methods for making an implantable device for delivering localized radiation in vivo. In one embodiment, a method of the invention includes loading a structure comprising a porous material with a heavy metal water-soluble salt dispersed throughout a substantial portion of the porous material, sterilizing the loaded structure, and packaging for storage and, optionally, delivery of the sterilized loaded structure. Preferably, the method of the invention further includes substantially contemporaneously loading a water soluble radiation emitting material, wherein a water insoluble radioactive salt is produced throughout a substantial portion of the porous material of the structure. "Substantially contemporaneously," means that the step of loading a water soluble radiation emitting material occurs at or near a step of positioning the device proximate to a desired localized in vivo area, i.e., at or near the surgical arena prior to administration to, preferably implantation in, a patient. More preferably, the water insoluble radioactive salt is dispersed throughout a substantial portion of the porous material.

In another embodiment according to the invention, a method includes loading a structure comprising a porous material with a heavy metal water-soluble salt dispersed throughout a substantial portion of the porous material; loading a water soluble radiation emitting material, wherein a water insoluble radioactive salt is produced in a substantial portion of the porous material of the structure; and packaging for delivery of the loaded structure.

Thus, the methods for making an implantable device to deliver radiation in vivo, in accordance with the invention, are versatile. A radiation emitting material may be loaded onto a structure including a porous material at any number of points between, and including, the point of manufacture and the point of use. As a result of one method, the device can be stored and transported prior to incorporation of the radiation emitting material. Thus, the end user can select the radioactive material to be used from a wider range of radioisotopes. For example, a radioisotope with a shorter half-life with certain particle emitting characteristics can be selected because the radioisotope is incorporated in situ, i.e., substantially contemporaneously to administration to a patient. The radioisotope selected is not limited to only those with long half-lives that may not be as effective for a particular therapy. Additionally, by providing a structure including a porous material having a radiation emitting material dispersed therein, the ability to deliver radiation from the radioactive material is predicted to be more uniform as compared to delivery with a device that does not include a porous material. It is believed that including a porous material provides a substantially consistent matrix for incorporation of a radiation emitting material over substantially an entire in vivo location in proximity to a device according to the invention.

BRIEF DESCRIPTION OF THE DRAWINGS

FIG. 1 is an elevational view of one embodiment of a device according to the invention with a balloon catheter as a mode of delivery of the device;

FIG. 2 is an elevational view of another embodiment of a device according to the invention with a balloon catheter as a mode of delivery of the device.

DESCRIPTION OF PREFERRED EMBODIMENTS

Figure 3:
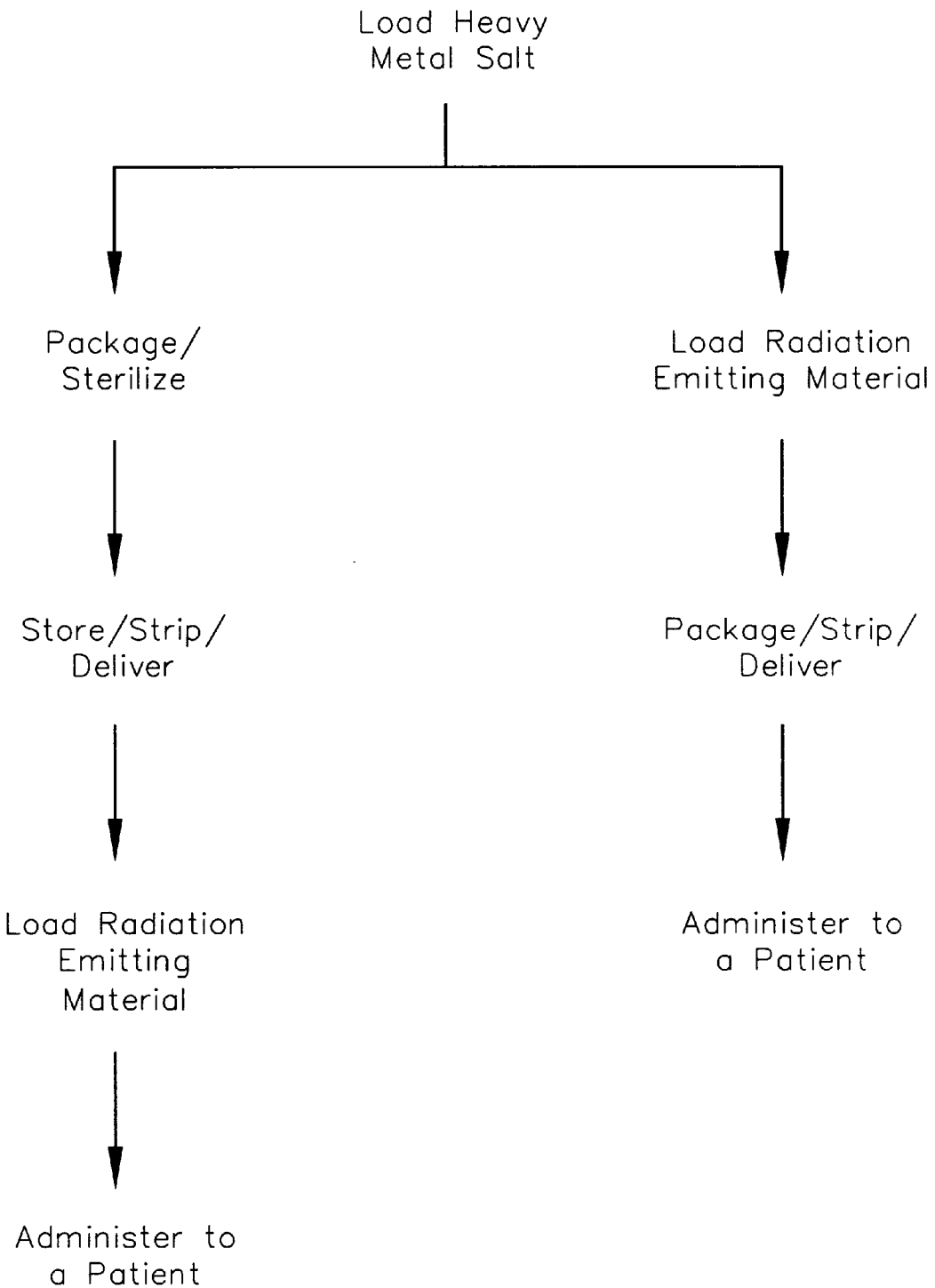
FIG. 3 is a flow diagram schematically illustrating methods according to the invention.

The present invention provides a device for delivering localized radiation in vivo including a structure comprising a porous material; and a plurality of discrete particles comprising a water-insoluble radioactive salt dispersed throughout a substantial portion of the porous material. Preferably, the structure includes a shape capable of delivering localized radiation to an internal human body site. In one embodiment, the shape is preferably generally cylindrical, more preferably the shape is selected from the group of a catheter, a stent, and a guide wire. In another embodiment, the shape is preferably generally sheet-like.

One more preferred shape is a stent which is a particularly useful shape in artery/vascular therapies. The term "stent"

refers to any device capable of being delivered by a catheter and which, when placed into contact with a portion of a wall of a lumen to be treated, will also deliver localized radiation at the lumen wall. A stent typically includes a lumen wall-contacting surface and a lumen-exposed surface. Where the stent is shaped generally cylindrical or tube-like, including a discontinuous tube or ring-like structure, the lumen-wall contacting surface is the surface in close proximity to the lumen wall whereas the lumen-exposed surface is the inner surface of the cylindrical stent. The stent can include polymeric or metallic elements, or combinations thereof, onto which a porous material is applied. For example, a deformable metal wire stent is useful as a stent framework of this invention, such as that described in U.S. Pat. No. 4,886,062 to Wiktor, which discloses preferred methods for making a wire stent. Other metallic stents useful in this invention include those of U.S. Pat. No. 4,733,665 to Palmaz and U.S. Pat. No. 4,800,882 to Gianturco.

Referring now to FIG. 1, the stent 20 comprises a stent framework 22 and a porous material coating 24. The stent framework 22 is deformable and can be formed from a polymeric material, a metal or a combination thereof. A balloon 16 is positioned in FIG. 1 adjacent the lumen-exposed surface of the stent to facilitate delivery of the stent. The stent 20 can be modified to increase or to decrease the number of wires provided per centimeter in the stent framework 22. Similarly, the number of wire turns per centimeter can also be modified to produce a stiffer or a more flexible stent framework.

Polymeric stents can also be used in this invention. The polymers can be nonbioabsorbable or bioabsorbable in part, or total. Stents of this invention can be completely nonbioabsorbable, totally bioabsorbable or a composite of bioabsorbable polymer and nonabsorbable metal or polymer. For example, another stent suitable for this invention includes the self-expanding stent of resilient polymeric material as disclosed in International Publication No. WO 91/12779.

Nonbioabsorbable polymers can be used as alternatives to metallic stents. The stents of this invention should not substantially induce inflammatory and neointimal responses. Examples of biostable nonabsorbable polymers that have been used for stent construction with or without metallic elements include polyethylene terephthalate (PET), polyurethane urea and silicone (for example, see van Beusekom et al. *Circulation* 86(supp. I):I-731, 1992 and Lincoff et al. *J Am. Coll Cardiol* 21(supp. 1):335A, 1994. Although the porous material is shown as a coating 24, it is to be understood that, for the purposes of this invention, the porous material can be incorporated into the material of the stent.

Referring to FIG. 2, an alternative stent 30 is shown. The stent framework 34 is affixed with a film of a porous material 32. This can be accomplished by wrapping the film 32 around the stent framework 34 and securing the film 32 to the framework 34 (i.e., the film is usually sufficiently tacky to adhere itself to the framework but a medical grade adhesive could also be used if needed) so that the film 32 will stay on the balloon 36 and framework 34 until it is delivered to the site of treatment. The film 32 is preferably wrapped over the framework with folds or wrinkles that will allow the stent 30 to be readily expanded into contact with the wall of the lumen to be treated. Preferably, the film 32 is located on a lumen-wall contacting surface 33 of the stent framework 34 such that radiation is substantially locally delivered to a lumen wall, for example, an arterial wall membrane (not shown).

Porous Material

As mentioned above, the device according to the invention is generally a structure including a porous material. In one embodiment, the porous material is a film on at least a portion of the structure. In another embodiment, the porous material is an integral portion of the structure. Preferably, the porous material is biocompatible, sufficiently tear-resistant and nonthrombogenic. More preferably, the porous material is selected from the group of a natural hydrogel, a synthetic hydrogel, teflon, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like. In materials which do not include pores in their usual structural configurations, pores between one micrometer in diameter or as large as 1000 micrometers in diameter can be introduced by conventional means such as by introducing a solvent soluble particulate material into the desired structure and dissolving the particulate material with a solvent. However, no particular pore size is critical to this invention.

Radiation Emitting Material

In selecting the appropriate isotope to use in forming the water-insoluble radioactive salt, several factors must be considered. For example, it is preferred that a low dose of radioactivity is delivered over a relatively long period of time in order to suppress the proliferative response to injury in vivo. Thus, total dose (generally measured in centi Gray) is typically determined by the specific activity of the radiation emitting material (generally measured in micro Curies ($\mu$Ci)) multiplied by time. However, the total dose must be balanced with the desired interruption of an injury response versus the detrimental mutagenic effect of tissue exposure to radiation. Thus, it is believed, for example, that $\beta$-radiation would be considered relatively high intensity radiation so that administration over a long period of time would not be beneficial. Preferably, the water-insoluble radioactive salt comprises $\beta$-radiation emitting isotope. More preferably, the $\beta$-radiation emitting isotope has an half-life of about 150 days or less. Most preferably, the water-insoluble radioactive salt is selected from the group of $AgI^{125}$, $BaS^{35}O_4$, and $(Ca)_3(P^{32}O_4)_2$. "Insoluble salt" or "water insoluble salt" of the radiation emitting material as set forth herein, means that the salt formed has a relatively poor solubility in water such that it will not readily disperse from the pores of the device.

Preferably, the water-insoluble radioactive salt is formed by a heavy metal water-soluble salt interacting with an aqueous radioactive salt solution. In the present invention, the heavy metal water-soluble salt is dispersed throughout a substantial portion of the porous material. Preferably, the heavy metal water-soluble salt is selected from the group of $AgNO_3$, $Ba(NO_3)_2$, $BaCl_2$, $CaCl_2$, and a mixture thereof. The amount of water-soluble salt dispersed throughout a portion of the porous material determines the ultimate amount of radiation capable of being emitted once the device is implanted.

Methods of Making an Implantable Device

Referring now to FIG. 3, a structure having a porous material is loaded with a heavy metal water-soluble salt. Preferably, this step includes contacting, more preferably immersing, the structure with an aqueous solution of the heavy metal water-soluble salt, as described above. Preferably, the heavy metal water-soluble salt is dispersed throughout a substantial portion of the porous material. The resulting structure can now be sterilized, packaged and, optionally, stored until use.

In one embodiment of the invention, a sterilized structure is shipped or delivered to the relevant consumer. The structure is substantially contemporaneously loaded with a water soluble radiation emitting material. Preferably, the loading of the radiation emitting material includes contacting, more preferably immersing, the porous material in an aqueous solution comprising a radioactive salt, as described above. Preferably, a water-insoluble radioactive salt is formed within the porous material. Examples of aqueous radioactive salt solutions include $NaI^{125}$, $K_2S^{35}O_4$, $NaS^{35}O_4$, and $Na_3P^{32}O_4$, to name a few.

This method is advantageous in that the structure is loaded with the radiation emitting material in situ, i.e., at or near the point of therapeutic use, typically before administration, preferably implantation, to a patient. This is particularly useful because the device can be stored and transported prior to incorporation of the radioactive material. This feature has several advantages. For example, the relevant consumer can select the radiation emitting material to be used from a wider range of radioisotopes, e.g., a radioisotope with a shorter half-life with certain particle emitting characteristics can be selected. Thus, the radioisotope selected is not limited to only those with long half-lives which may not be as effective for a particular therapy.

In another embodiment, a sterilized structure is loaded with a radioactive emitting material. Preferably, the loading of the radiation emitting material includes contacting, more preferably immersing, the porous material in an aqueous solution comprising a radioactive salt, wherein a water-insoluble radioactive salt is formed within the porous material. Examples of aqueous radioactive salt solutions may be those previously mentioned above. The structure is preferably packaged and can shipped to the relevant consumer. The structure can now be administered, preferably implanted, to a patient. Thus, in this embodiment, the structure is loaded with the radiation emitting material prior to reaching the point of use, which may be more convenient depending upon the facilities available to the relevant consumer.

EXAMPLE

The following non-limiting example will further illustrate the invention. All parts, percentages, ratios, etc. are by weight unless otherwise indicated.

The following solutions were used in the procedure:

Solution A: 1–10% aqueous solution of $BaCl_2$

Solution B: 1–10% aqueous solution of $Ba(NO_3)_2$

Solution C: 1–10% aqueous solution of $Na_2S^{35}O_4$

A gamma-radiation sterilized porcine fibrin stent made according to U.S. Pat. No. 5,510,077 was treated by rehydration in Solution A by immersion for about 5 to about 10 minutes. The stent was removed and excess solution was blotted with absorbent paper. The stent was then dehydrated and sterilized by gamma radiation.

This treated stent was then rehydrated in an aqueous solution of $Na_2S^{35}O_4$ radioisotope having a specific activity of about $10\mu$ Ci/ml to about $500\mu$ Ci/ml. A white precipitate of $BaS^{35}O_4$ was observed within the pores of the stent surface. The stent can now be implanted into an artery for localized delivery $\beta$-radiation or packaged for delivery to the consumer.

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

What is claimed is:

1. An implantable device capable of delivering localized radiation in vivo comprising:

a structure comprising a porous material; and a plurality of discrete particles comprising a heavy metal water-soluble salt dispersed throughout a substantial portion of the porous material, wherein the heavy metal water-soluble salt forms a water insoluble salt containing a radiation emitting material upon contact with a solution of a radioactive salt.

2. The implantable device of claim 1, wherein the porous material comprises a material selected from selected from the group of a natural hydrogel, a synthetic hydrogel, teflon, silicone, polyurethane, polysulfone, cellulose, polyethylene, polypropylene, polyamide, polyester, and polytetrafluoroethylene.

3. The implantable device of claim 1, wherein the radiation emitting material comprises a $\beta$-radiation emitting isotope.

4. The implantable device of claim 1, wherein the heavy metal water-soluble salt is selected from the group of $AgNO_3$, $Ba(NO_3)_2$, $BaCl_2$, and $CaCl_2$.

5. The implantable device of claim 1, wherein the structure comprises a generally cylindrical shape.

6. The implantable device of claim 5, wherein the shape is selected from the group of a catheter, a stent, and a guide wire.

7. The implantable device of claim 1, wherein the $\beta$-radiation emitting isotope has an half-life of about 150 days or less.

8. The implantable device of claim 7, wherein the water-insoluble radioactive salt is selected from the group of $AgI^{135}$, $BaS^{35}O_4$, and $(Ca)_3(P^{32}O_4)_2$.

* * * * *